US008385624B2

United States Patent
Charlot et al.

(10) Patent No.: US 8,385,624 B2
(45) Date of Patent: Feb. 26, 2013

(54) AUTOMATED TRANSIENT IMAGE CYTOMETRY

(76) Inventors: David J. Charlot, La Jolla, CA (US); Randall S. Ingermanson, Battleground, WA (US); Patrick M. McDonough, San Diego, CA (US); Jeffrey H. Price, Rancho Santa Fe, CA (US)

(*) Notice: Subject to any disclaimer, the term of this patent is extended or adjusted under 35 U.S.C. 154(b) by 576 days.

(21) Appl. No.: 12/454,217

(22) Filed: May 13, 2009

(65) Prior Publication Data

US 2010/0289887 A1 Nov. 18, 2010

(51) Int. Cl.
  *G06K 9/20* (2006.01)
(52) U.S. Cl. ............ 382/133; 382/283; 348/79
(58) Field of Classification Search .......... 382/133, 382/283
  See application file for complete search history.

(56) References Cited

U.S. PATENT DOCUMENTS

| 6,400,487 | B1* | 6/2002 | Harris et al. ............... 359/210.1 |
| 6,682,927 | B2 | 1/2004 | Meyer et al. ............... 435/288.7 |
| 7,655,434 | B2 | 2/2010 | Jones et al. ............... 435/29 |
| 2005/0233356 | A1 | 10/2005 | Jones et al. ............... 435/6.11 |
| 2006/0147901 | A1 | 7/2006 | Jan et al. ............... 435/4 |
| 2007/0016373 | A1 | 1/2007 | Hunter et al. ............... 702/19 |
| 2008/0144895 | A1 | 6/2008 | Hunter et al. ............... 382/128 |
| 2011/0318775 | A1 | 12/2011 | Mercola et al. ............... 435/32 |

FOREIGN PATENT DOCUMENTS

WO   WO 2007061971 A2 *  5/2007

OTHER PUBLICATIONS

Teruel, M.N. and Meyer, T., Parallel single-cell monitoring of receptor-triggered membrane translocation of a calcium-sensing protein module. *Science*, 2002;295:1910-1912.
Bers, D.M. Cardiac excitation-contraction coupling. *Nature*. 2002;415:198-205.
Mummery, C., Ward-van Oostwarrd, D., et al. Differentiation of Human Embryonic Stem Cells to Cardiomyocytes: Role of Coculture with Visceral Endoderm-Like Cells. *Circulation*. 2003;107:2733-2740.
Mery, A., Aimond, F., et al. Initiation of Embryonic Cardiac Pacemaker Activity by Inositol 1,4,5-Triphosphate-dependent Calcium Signaling. *Mol. Bin. of the Cell*. 2005;16:2414-2423.
Grey, C., Mery, A., et al. Fine-tuning homeostasis underlies progression of cardiomyopathy in myocytes derived from genetically modified embryonic stem cells. *Hum. Mol. Gen*. 2005;14,10:1367-1377.
Dolnikov, K., Shilkrut, M., et al. Functional properties of human embryonic stem cell-derived cardiomyocytes. *Ann. N.Y. Acad. Sci*. 2005;1047:66-75.
Fast, V. Simultaneous optical imaging of membrane potential and intracellular calcium. *J. of Elect*.2005; 38:107-112.

* cited by examiner

*Primary Examiner* — Wensing Kuo
(74) *Attorney, Agent, or Firm* — Terrance A. Meador; INCAPLAW

(57) ABSTRACT

A method, system, and instrument for automatically measuring transient activity in cells uses image time sequences to identify transients in cells. Preferably, the transient activity is stimulated or provoked in synchronism with acquisition of the image time sequences. A cell mask is applied to each image of an image time sequence in order to localize the transient activity with respect to each cell. Localization enables cell-by-cell analysis of properties of the transient activity.

5 Claims, 7 Drawing Sheets

AUTOMATED TRANSIENT IMAGE CYTOMETRY

STATEMENT OF GOVERNMENT INTEREST

The invention described herein were made in part with government support under Grant No. 1R42HL086076 awarded by the National Institutes of Health. The United States Government has certain rights in the invention.

RELATED APPLICATIONS

This Application contains subject matter related to the subject matter of the assignee's U.S. patent application Ser. Nos. 11/285,691, filed Nov. 21, 2005, and published as US 2008/0144895 A1 on Jun. 19, 2008, and to the PCT counterpart, PCT/2005/044936, filed Nov. 17, 2006, and published as WO 2007/061971 A2 on May 31, 2007.

BACKGROUND

The field is processes, systems, and instruments for automatically measuring transient activity in cells using image sequences. More specifically, the field includes use of image cytometry to automatically measure calcium transients in cardiomyocytes.

Automated image cytometry is increasingly used in high content screening (HCS) to automatically measure characteristics of objects in magnified images of cellular material. Typically, an automated image cytometry system includes tools to perform analysis of images and analysis of data acquired from the images. Image analysis may include staining material with one or more dyes, each selected to bind with a particular structure or component of the material. For example samples in a multi-well screening experiment related to obesity may be stained with one dye that binds specifically with cell nuclei, a second dye that binds specifically with cell cytoplasm, and a third dye that binds with lipid droplets. Magnified images of well contents may be selectively processed according to color in order to classify image objects such as nuclei, cell perimeters, and lipid droplets. Once classification is complete, data may be extracted from the classification results in order to quantify various properties of the objects. See, for example the related US publication 2008/0144895 A1.

Heart failure due to hypertension, infarction, or other factors, is a leading killer of men and women in modern society and involves, at its base, a debilitating loss of cardiomyocytes. Encouraging recent studies indicate the feasibility of regenerating lost cardiomyocytes, for example by transplanting embryonic stem cell-derived cardiac myocytes (ESCMs) or mobilizing resident stem cells. To realize the potential of stem-cell based therapies, it would be extremely beneficial to develop technology and instruments for high throughput, high content screening (HCS) of drugs and genes for their ability to stimulate the formation of functional, contractile cardiomyocytes.

Figure 1:
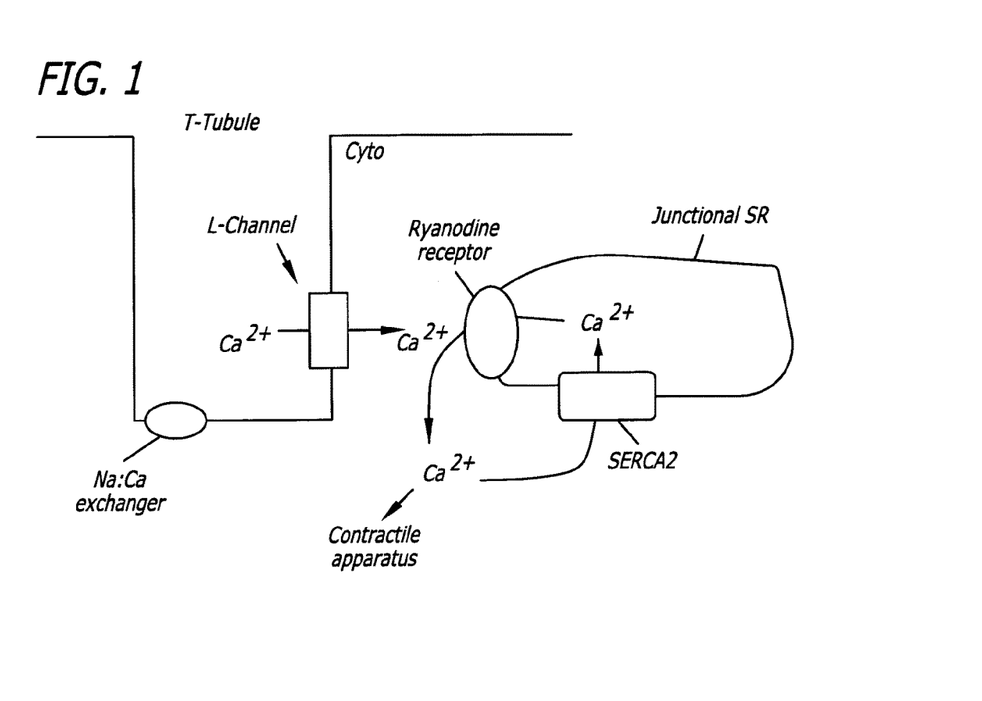
FIG. 1 illustrates a model of the cardiomyocyte contractile mechanism.
Figure 2:
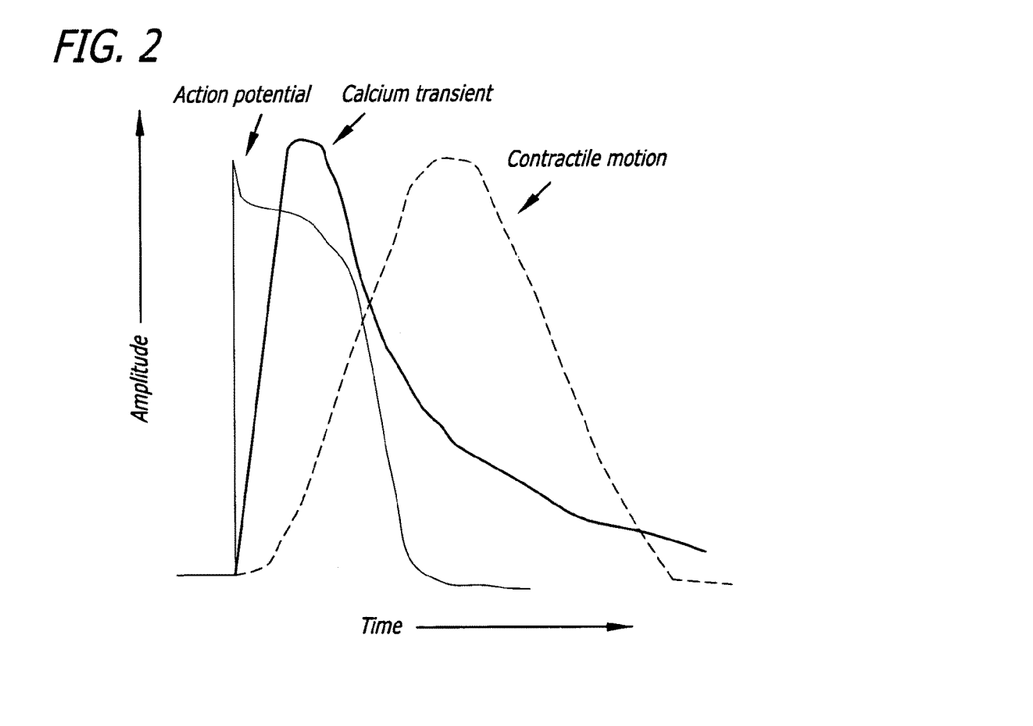
FIG. 2 is a plot of the cardiac contractile cycle per the model of FIG. 1.

The contractile cycle of cardiomyocytes shown in FIGS. 1 and 2 (adapted from Donald M. Bers, "Cardiac excitation-contraction coupling," *Nature*, Vol 415, pp: 198-205, 2002) is divided into an abrupt shortening phase (systole), induced by a rapid rise in the intracellular calcium concentration ($[Ca^{2+}]_i$) due to calcium entry via voltage dependent L-type calcium channels and calcium-induced-calcium release from the sarcoplasmic reticulum (SR). Contraction is followed by relaxation of the cell (diastole) and the decline of $[Ca^{2+}]_i$. Decline of $[Ca^{2+}]_i$ during diastole is controlled primarily by re-sequestration of calcium back into the SR by SERCA2, an ATPase associated with the SR membrane.

Calcium transients have been recorded from cardiomyocytes derived from embryonic stem cells (both from mouse and from human). For example, calcium transients in fura-2-loaded cardiomyocytes derived from human embryonic stem cells (hESC-CM), were observed in spontaneously contracting embryoid bodies [K. Dolnikov, et al., "Functional Properties of Human Embryonic Stem Cell-Derived Cardiomyocytes," *Ann. N.Y. Acad. Sci.* 1047, pp: 66-75, 2005]. hESC-CMs cultured on mouse visceral-endoderm like cells showed similar calcium transients and spontaneous contractions at 0.6 to 1.5 Hz [Mummery et al., "Differentiation of Human Embryonic Stem Cells to Cardiomyocytes," *Circulation*. 107, pp: 2733:2740, 2003]. Fluo-4 (a fluorescent dye) has been used to record calcium transients from murine ESCMs, which exhibited spontaneous contraction rates of approximately 1 Hz [Grey, et al., "Fine-tuning in $Ca^{2+}$ homeostasis underlies progression of cardiomyopathy in myocytes derived from genetically modified embryonic stem cells," *Human Molecular Genetics* 14(10), pp: 1367-1377, 2005]. Consistent with the wide spread observation of spontaneous beating in experiments designed to elicit the appearance of ESCMs, myocytes with "pace-maker" activity have been observed in contracting cell clusters, serving to drive the contractions of neighboring cells [Mery et al., "Initiation of Embryonic Cardiac Pacemaker Activity by Inositol 1,4,5-Trisphosphate-dependent Calcium Signaling," *Mol Biol Cell*, 16(5), pp: 2414-23, 2005]. These studies indicate that ESCMs typically exhibit calcium transients and contractile characteristics similar to neonatal rat ventricular myocytes (NRVMs), rather than adult cardiomyocytes.

Automated high content screens allow for a wealth of information to be gathered from a given experimental study. If the hardware and controlling software are present, researchers may be able to fine tune hardware performance to directly match their experimental needs. Unfortunately, this is not always the case and researchers are usually forced to either tweak their experimental design or are required to build customized tools to conduct their experiments. Thus, it would be extremely desirable to be able to record $Ca^{++}$ transients on a cell-by-cell basis in a manner that is easily integrated into current laboratory setups. A desirable Calcium Transient Image Cytometer (CTIC) would interface easily into available high content microscopy workstations which already perform multi-well plate scanning and image acquisition, to enable video burst acquisition and analysis of calcium transients in a fully automated (high throughput screening) mode. It is desirable that the CTIC electrically stimulate (or pace) the cells, record the resulting $Ca^{++}$ transients from cells in microtiter plates (e.g., with 96 wells), and automatically quantify characteristics such as the duration of the $Ca^{++}$ waves on a cell-by-cell basis in a fully automated manner on large scale screens (e.g., tens to hundreds of thousands of compounds).

SUMMARY

A method, system, and instrument for automatically measuring transient activity in cells uses image time sequences to identify transients in cells. Preferably, the transient activity is stimulated or provoked in synchronism with acquisition of the image time sequences. A cell mask is applied to each image of an image time sequence in order to localize the transient activity with respect to each cell. Localization enables cell-by-cell analysis of properties of the transient activity.

Figure 3:
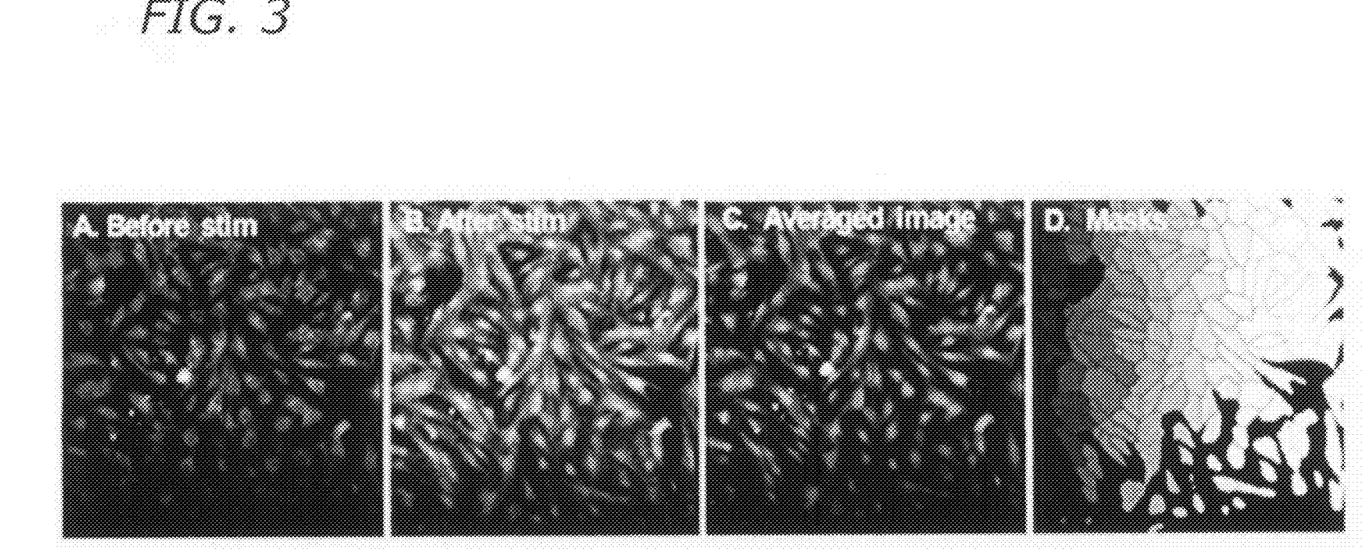
FIG. 3 is a sequence of images with the same field of view that illustrates a method for obtaining segmented cell masks from a video stream constituted of a time-series sequence of magnified images.

DETAILED DESCRIPTION OF THE PREFERRED EMBODIMENTS in order to obtain information about a transient event (like the contractile cycle of cardiomyocytes) on a cell-by-cell basis in an automated image cytometry system, a video stream constituted of time-sequenced magnified images is acquired and an averaged image is obtained from averages of all images in the video stream. The averaged image is segmented to obtain a cell periphery mask. A set of transient data for each cell is obtained by applying the mask to each image of the video stream. For example, but without limiting the scope of application, presume a video stream of magnified images is obtained which is constituted of a time-series sequence of frames containing magnified images of the same field of view showing cells marked with a dye bound to elements active in a transient event. For example, presume that the time-series sequence includes magnified images of fluo-4 loaded cardiac myocytes. With reference to FIG. 3, the time-series sequence of frames includes images A and B, among other images. Image A is a raw image of NRVMs prior to stimulation of a $Ca^{++}$ transient by application of an electrical signal (low $Ca^{++}$, dim fluo-4). Image B is an image with the same field of view as Image A, but later in time, immediately after stimulation, when $Ca^{++}$ is high and fluo-4 is bright. All of the images in the video stream are averaged to obtain the averaged image denoted as Image C. Using known algorithms, cell periphery masks are segmented from the averaged image. The segmented masks are illustrated in Image D wherein each cell mask is labeled with a unique gray-scale intensity for illustration of this description.

Figure 4:
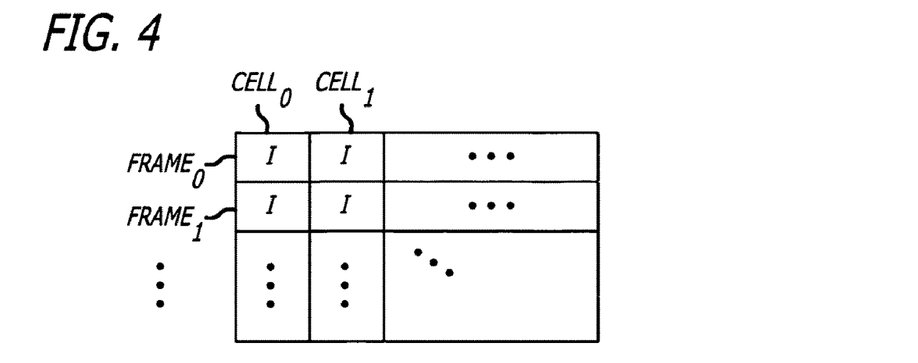
FIG. 4 data table illustrating storage of data obtained from a video stream constituted of a time-series sequence of magnified images using cell masks.

Once a cell periphery mask is generated, it is applied to each image in the time-series sequence of images at the location of the cell it represents and the fluo-4 intensity within the mask is measured and recorded. As per FIG. 4, showing tabular recording of intensity data for illustration only, each row in the table represents a frame (or image) in the video sequence where an image is obtained and each column represents a cell. Thus, each data entry in a column represents the fluo-4 intensity (I) of the corresponding cell at a particular time of a $Ca^{++}$ transient.

Figure 5:
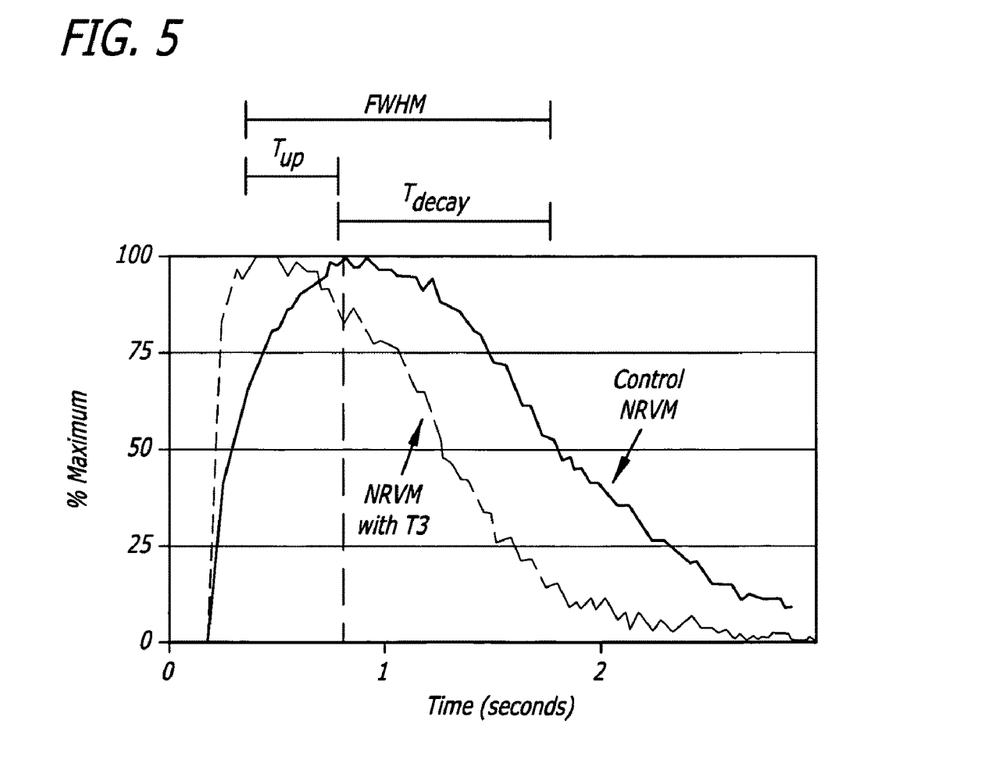
FIG. 5 is a plot of transient curves made using data obtained from a video stream constituted of a time-series sequence of magnified images using cell masks.

The intensity data points for a cell may be processed by known means to yield corresponding transient magnitude points which, in turn, may be used to plot a $Ca^{++}$ transient for the cell. Transients plotted using such data points are shown in FIG. 5 for a control NRVM and for a NRVM maintained in 100-nM thyroid hormone. The transients are normalized to their minimum (0%) and maximum values (100%). Kinetic parameters which may be derived from the transients include Full Width at Half Max (FWHM) which is the time required for progression from the 50% point on the upstroke to 50% point on the downstroke, $T_{up}$, which is the time from the 50% point to 100% on the upstroke, and $T_{decay}$, which is the time period from the 100% point to the 50% point on the decay phase.

Figure 6:
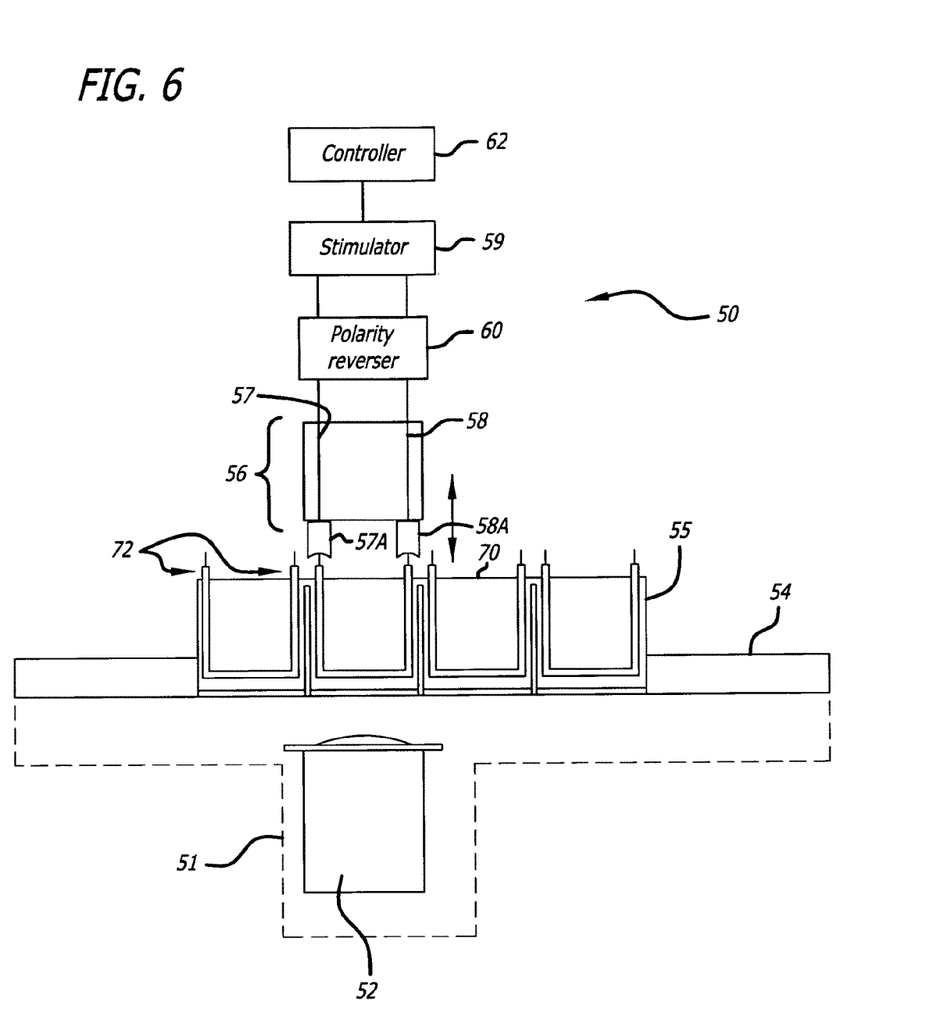
FIG. 6 is a partially schematic illustration of an instrument for acquiring a time-series sequence of magnified images from a multi-well plate or dish.

An instrument illustrated in the schematic block diagram of FIG. 6 may be used to acquire one or more video streams for processing images as illustrated in FIG. 3. The instrument 50 includes a robotic inverted microscope 51 outfitted for fluorescent microscopy. The microscope 51 has an objective 52 and a mechanical stage 54 adapted to support a multi-well plate or dish. Conventional stage control mechanization causes the mechanical stage 54 to be moved in three dimensions. The stage control mechanization causes the mechanical stage 54 to move in a predetermined pattern to bring wells of a multi-well plate or dish into position in the field of view of the microscope objective 52; when a well is positioned in the field of view of the objective 52, the stage control mechanization moves the stage vertically for autofocus; the autofocus position is held while a video clip is obtained. The mechanical stage 54 is conventionally adapted to support a multi-well plate or dish for being moved with respect to the field of view of the objective 52. Such a plate may be one constructed with a transparent bottom so that the contents of its wells are visible to the objective 52. For example, a glass-bottomed 96-well plate 55 may be used.

When transient activity analysis requiring stimulation of well contents is to be conducted, the instrument of FIG. 6 may be further adapted to accommodate the requirement. Such accommodation may support stimulation of well contents by light, pressure, electrical potential, material, and so on. In addition, a multi-well plate may be adapted to couple such stimulation to its wells. For example, it may be desirable to stimulate cells by application of an electrical voltage. In this case, the instrument of FIG. 6 may be adapted by provision of a coupling electrode assembly 56 mounted on a moveable arm that moves the coupling electrode assembly vertically with respect to the objective 52. Control mechanization for positioning the coupling electrode assembly 52 may be conventional. That is to say, a control mechanization for positioning the moveable arm to which the coupling electrode assembly 52 is mounted may include, for example, a motor and a control routine for operating the motor to move the arm when the coupling electrode assembly 52 is to be raised or lowered. The coupling electrode assembly 56 includes electrically conductive electrodes 57 and 58 disposed in a spaced parallel relationship. A stimulator 59 applies a voltage across the electrodes 57 and 58 and a polarity reverser 60 reverses the polarity of the voltage. In some aspects, the stimulator 59 and polarity reverser 60 are constructed to operate in response to a controller 62 by causing the electrodes 57 and 58 to deliver one or more shaped stimulus signals. In some aspects, the shaped stimulus signals may be pulses (preferably rectangular in shape) of electrical voltage.

The instrument of FIG. 6 may couple electrical stimulation to the contents of wells in a multi-well plate or dish by moving the electrodes 57 and 58 into and out of each well positioned in the field of view of the objective 52. However, the electrodes might have to be cleaned after being withdrawn from a well so as not to contaminate the contents of the next well. According to an alternate embodiment, each well may be provided with a set of electrodes that are adapted to couple to the electrodes 57 and 58 so that no set of electrodes enters more than a single well. This solution is illustrated in FIG. 6 by a lid for a multi-well plate or dish. In this regard, a lid 70 seats on the top of the glass-bottomed 96-well plate 55. The lid 70 has multiple pairs of lid electrodes 72 mounted to it, each pair being positioned to extend into a respective well when the lid 70 is seated on the top of the plate 55. The lid electrode pairs 72 extend fully into their respective wells and protrude above the lid 70; preferably, they are flexible, electrically conductive elements and may be retained in place at least partially by spring loading. The electrodes of each pair of lid electrodes 72 are retained by the lid in the spaced parallel relationship of the electrodes 57 and 58 so that when a well is positioned in the field of view of the objective 52, the electrodes 57 and 58 are longitudinally aligned with the lid electrode pair for that well. Lowering the coupling electrode assembly 56 carries the electrodes 57 and 58 into electrical contact with the lid electrode pair of the positioned well; raising the assembly carries the electrodes 57 and 58 out of contact and permits the plate 55 to be repositioned. In some aspects, the electrodes 57 and 58 may include respective end receptacles 57A and 58A shaped to facilitate coupling to lid electrode pairs. For example, the end receptacle of each coupling electrode may be shaped with a wide mouth and an internal tapered cone to capture and make electrical contact with flexible and spring-loaded lid electrode tips that protrude above the lid.

Figure 7:
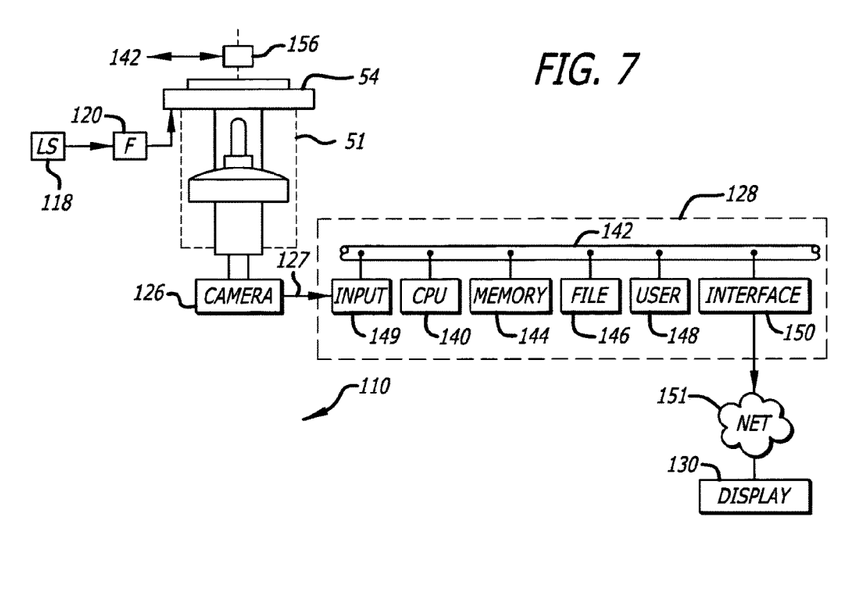
FIG. 7 is a block diagram of a system for performing a computer-executed method of automated transient image cytometry.

FIG. 7, which is meant for example and not for limitation, illustrates an automated image cytometry system adapted to perform automated transient image cytometry. The system is adapted by addition of programming for the video stream processing illustrated in FIG. 3 to the automated image cytometry programming and by addition of the instrumentation illustrated in FIG. 6. The system performs a computer-executed method of automated transient image cytometry according the Detailed Description and which may be implemented in part in a software program, for example, a program written in the C++ and/or Java programming languages, and a counterpart system may be a special purpose computer system designed to execute the method. Of course, the method and the programmed computer system may also be embodied in a special purpose processor provided as a set of one or more chips. Further, there may be a program product constituted of a program of computer or software instructions or steps stored on a tangible article of manufacture that causes a computer to execute the method. The tangible article of manufacture may be constituted of one or more real and/or virtual data storage articles.

In FIG. 7 the automated instrumentation system is constructed and programmed to perform automated image processing, image data management, and image data analysis operations of HCS and/or HTS systems. For example, the instrumentation system may be, or may reside in, or may be associated with a microscopy system 100 including the microscope 51 with the motorized, automatically moveable stage 54 on which a carrier with biological material may be disposed for observation by way of the microscope 51. The carrier may be the multi-well plate 55 discussed above whose wells are disposed in a two dimensional array. For example, and without limitation, the multi-well plate 55 may be a ninety-six well micro-titer plate in each well of which there is biological material that has been cultured, activated, fixed, and stained. A light source 118 provides illumination for operation of the microscope 51 by way of an optical filter 120 and a fiber optic cable 122. The moveable stage 112 may be intermittently or continuously moved to enable the acquisition of one or more video streams each constituted of a time-series sequence of magnified images. Images in the field of view of the objective 52 are directed by mirrors and lenses to a high-resolution digital camera 126. The camera 126 obtains and buffers video streams and transfers them on an interface 127 to a processor 128. The interface 127 may be, for example and without limitation, a universal serial bus (USB). The frames of each video stream is are constituted of digital images which may be provided in some standard format comprising an N×M array of pixels to the processor 128. The processor 128 receives the digital images and stores them in image files. The digital images are processed by the processor 128 and output digital images may be provided by the processor 128 for display on an output device with a display 130.

With further reference to FIG. 7, the processor 128 may be a programmed general purpose digital processor having a standard architecture, such as a computer work station. The processor 128 includes a processing unit (CPU) 140 that communicates with a number of peripheral devices by way of a bus subsystem 142. The peripheral devices include a memory subsystem (MEMORY) 144, a file storage subsystem (FILE) 146, user interface devices (USER) 148, an input device (INPUT) 149, and an interface device (INTERFACE) 150. It is not necessary that the processor 128 be connected directly to the microscope 51; it may receive images produced by the camera 126 from a portable storage device, or by way of a local or wide area network. For example, images may be transported to the processor 128 over the internet.

The bus subsystem 142 includes media, devices, ports, protocols, and procedures that enable the processing unit 140 and the peripheral devices 144, 146, 148, 149, and 150 to communicate and transfer data. Instrumentation 156 such as is illustrated in FIG. 6 may also be coupled to the bus subsystem 142 by a conventional instrumentation interface. The bus subsystem 142 provides generally for the processing unit and peripherals to be collocated or dispersed The memory subsystem 144 includes read-only memory (ROM) for storage of one or more programs of instructions that implement a number of functions and processes. One of the programs is an automated image process for processing a magnified image of biological material to identify one or more components of an image. The memory subsystem 144 also includes random access memory (RAM) for storing instructions and results during process execution. The RAM is used by the automated image process for storage of images generated as the process executes. The file storage subsystem 146 provides non-volatile storage for program, data, and image files and may include any one or more of a hard drive, floppy drive, CD-ROM, and equivalent devices The user interface devices 148 include interface programs and input and output devices supporting a graphical user interface (GUI) for entry of data and commands, initiation and termination of processes and routines and for output of prompts, requests, screens, menus, data, images, and results.

The input device 149 enables the processor 128 to receive digital images directly from the camera 126, or from another source such as a portable storage device, or by way of a local or wide area network. The interface device 150 enables the processor 128 to connect to and communicate with other local or remote processors, computers, servers, clients, nodes and networks. For example, the interface device 150 may provide access to an output device 130 by way of a local or global network 151.

FIGS. 8-11 illustrate a software program containing instructions for operating a system such as that shown in FIG. 7 to perform a computer-executed method of automated transient image cytometry. An overview of an automated transient image cytometry method is seen in FIG where, at 200, the system initiates method at 200. The system acquires one or more video streams of cells exhibiting transient activity from one or more wells in a multi-well pate or dish at 202. At 204, at least one cell periphery mask is generated for each well where a video stream is acquired. Cytometric analysis using data generated with the cell periphery masks is performed at 206, and the method terminates at 207.

Figure 8:
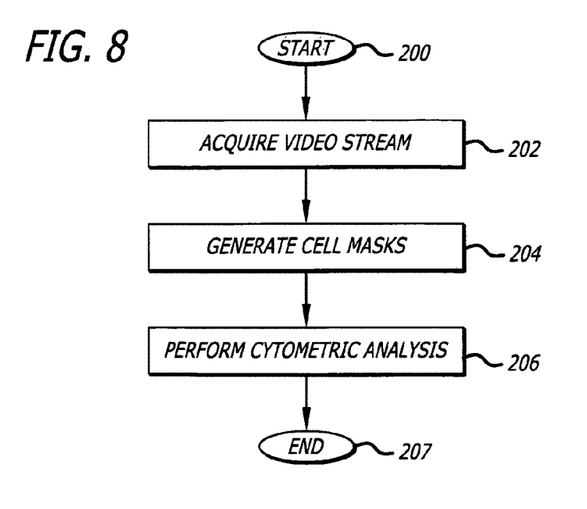
FIG. 8 is a flow chart illustrating a software program for performing a computer-executed method of automated transient image cytometry.
Figure 9:
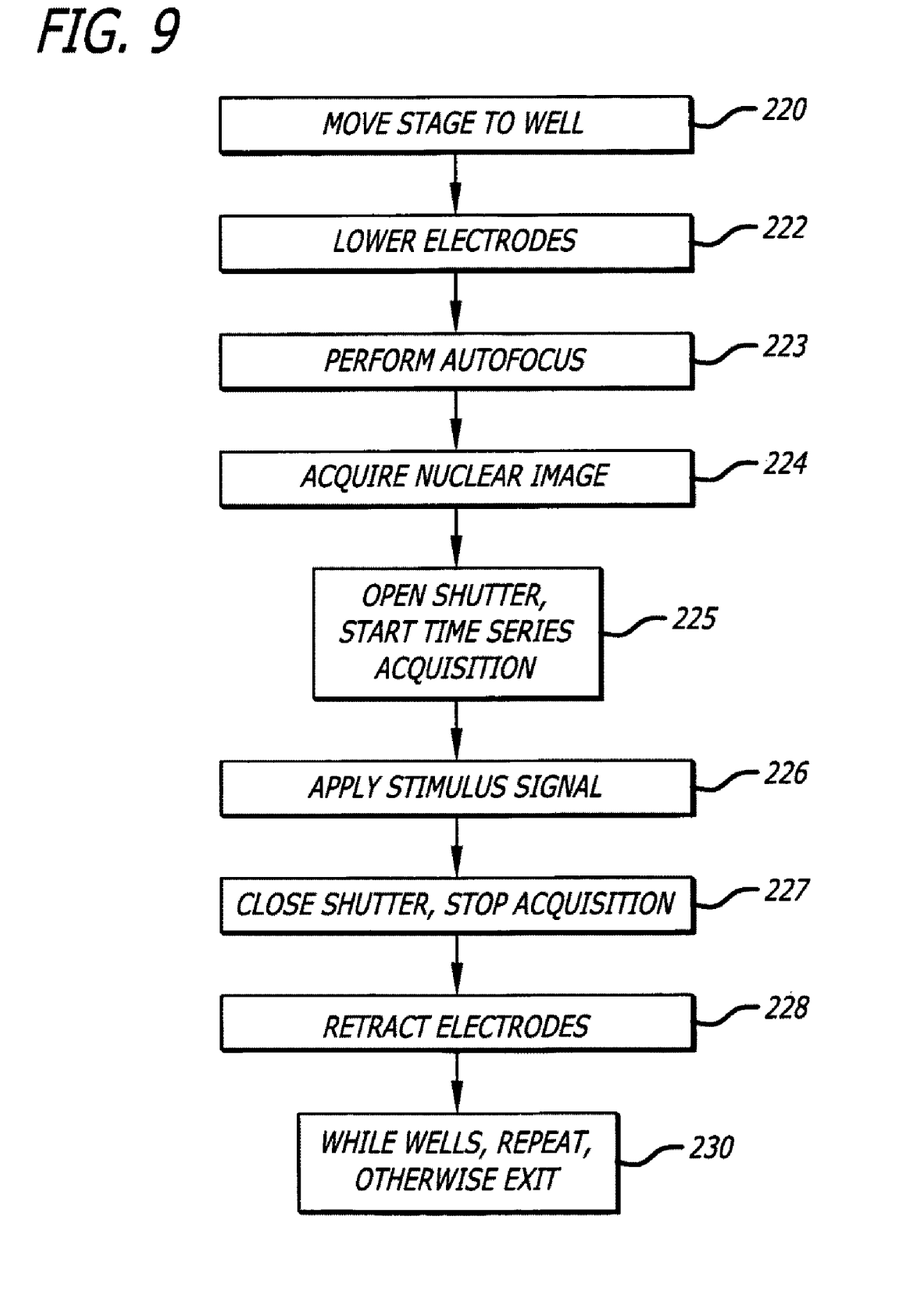
FIG. 9 is a flow chart illustrating an image acquisition phase of the software program of FIG. 8.

The acquisition of one or more video streams in step 202 of FIG. 8 is illustrated in more detail in FIG. 9, which is explained with reference to the instrument of FIG. 6. At 220, the mechanical stage 54 is moved to place a well in the field of view of the objective 52. At 222, the electrodes 57 and 58 are lowered to provide a stimulus signal to the well. Using the stained nuclei of cells in the well, an autofocus process adjusts the mechanical stage 54 vertically to a best focus position where the contents of the well are best focused by the objective 52. Then, at 224, with best focus established, a first filter is utilized to allow the objective 52 to image cell nuclei and a nuclear image is acquired and stored. At 225, using a second filter to establish a channel of interest, the camera shutter is operated to start acquisition of a video stream constituted of a time-series sequence of magnified images of objects in the well's contents. In this regard the channel of interest may be associated with or determined by the color of objects viewed through the second filter. Immediately thereafter, at 226, a stimulus signal is applied to the well in order to initiate transient activity in cells contained in the well. A time-series sequence of images of the cells, including those cells exhibiting transient activity, is captured in the ongoing video stream. After a predetermined amount of time sufficient to capture the transient event, the camera shutter is operated to cease acquisition. At 228, the electrodes are retracted and the time-series sequence of images is stored for later processing. At 230, as long as there is another from which to acquire a video stream, the process repeats; otherwise, the process ends.

Figure 10:
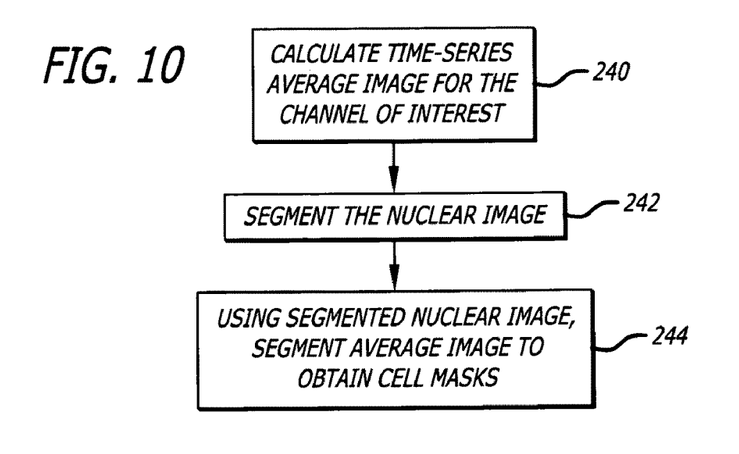
FIG. 10 is a flow chart illustrating an image segmentation phase of the software program of FIG. 8.

After acquiring a time-series sequence of images of the contents of a well, the system initiates cell mask generation as per FIG. 10. At 240, a time-series average image (per FIG. 3) is obtained using the channel of interest. At 242, the nuclear image for the well is segmented and the segmented nuclear image is used with the time-series average image to obtain cell masks at 244. Generation of cell masks may be done using a known technique such as a watershed algorithm.

Figure 11:
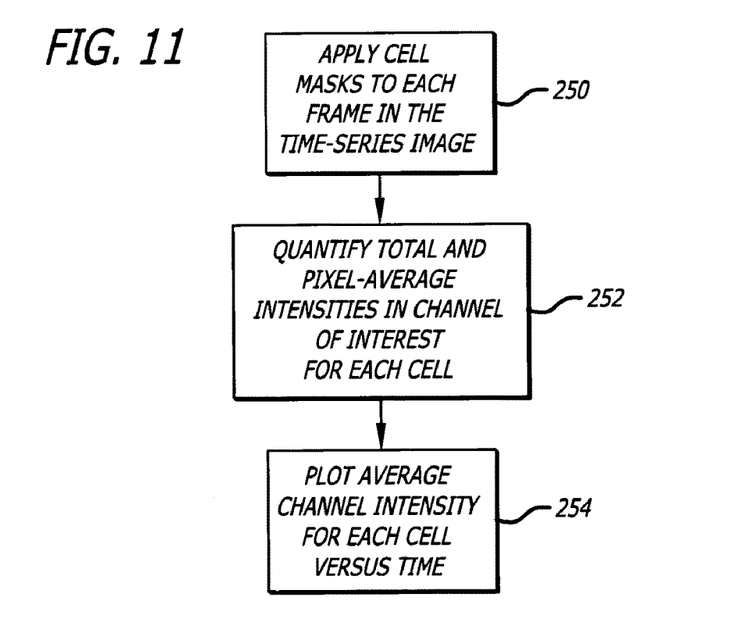
FIG. 11 is a flow chart illustrating a cytometric analysis phase of the software program of FIG. 8.

After acquiring cell masks for a time-series sequence of images of the contents of a well, the system initiates cytometric analysis as per FIG. 11. At 250, the cell masks are applied to each frame of the time-series sequence of images and total and average intensity magnitudes for each cell are obtained at 252 using the cell masks. At 254, the system may produce a plot showing average channel intensity versus time for each cell in the well as illustrated in FIG. 5.

Figure 12:
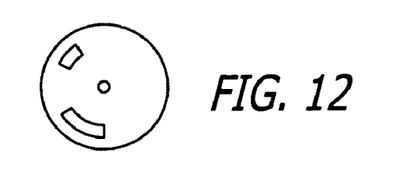
FIG. 12 is an illustration of a tangible medium of storage of a software program for operating an automated transient image cytometry system to perform a computer-executed method of automated transient image cytometry.

Methods and apparatuses for practicing these teachings may be constituted in whole or in part of a program product with a computer-readable storage medium, network, and/or node that enables a computer, a processor, a fixed or scalable set of resources, a network service, or any equivalent programmable real and/or virtual entity to execute an automated transient image cytometry process as described and illustrated above. The program product may include a portable medium suitable for temporarily or permanently storing a program of software instructions that may be read, compiled and executed by a computer, a processor, or any equivalent article. For example, the program product may include a programmed CD such as is seen in FIG. 12, or a network-accessible site, node, center, or any equivalent article.

INDUSTRIAL EXAMPLES

Cultured NRVMs were utilized according to the description and illustrations above to obtain the images of FIG. 3 and the plots of FIG. 5. These can be prepared quickly (as opposed to the more lengthy culturing required for ESCMs). The cultured NRVMs respond to electrical stimulation a $Ca^{++}$ transient accompanied by a contractile-twitch. The contractile calcium transients are transient elevations in intracellular calcium, which can be tracked via use of intracellular fluorescent calcium indicators (e.g., Fluo-3 and Fluo-4) and digital fluorescence microscopy technology as represented by the EIDAQ 100 (Q3DM, San Diego, Calif.) modified to obtain and process video streams as illustrated in FIGS. 3 and 4. An instrument designed to electrically stimulate, record, and quantify contractile calcium transients from NRVMs cultured in 96-well dishes, should be capable of recording electrically stimulated contractile calcium transients in cultures of embryonic stem cells to provide a definitive readout of the stage of differentiation towards cardiomyocytes. That is, we hypothesize that different stages of differentiation will be characterized by measurement differences in the $Ca^{++}$ transients of these beating cells. The instrument will also likely be useful for testing compounds on NRVMs (or cardiac myocytes from other sources) in a high throughput manner for potential negative or positive inotropic effects, or for arrhythmic effects.

The NRVMs were cultured in 96-well dishes (Nunc coverslip-glass-bottom plates) pretreated with 1% gelatin that was cross linked with glutaraldehyde to improve cell adherence.

Sensitivity to intracellular calcium kinetics is a desirable goal for automated calcium transient image cytometry because it is desirable to distinguish healthy contractile ESCMs from background non-contractile stem cells. To test this sensitivity, contractile calcium transients were quantified in two populations of NRVMs: NRVMs exposed to control media vs. media supplemented with 100-nM thyroid hormone (T3), which is known to increase the expression of SERCA2, leading to more rapid calcium re-uptake, and, overall accelerated kinetics of the contractile calcium transients (FIG. 5). Thus, for all NRVMs preparations, half of the wells contained control medium (DMEM: F12 with 0.25% FBS) and the remainder included the same media supplemented with T3. The cells were maintained 48 to 72 hrs prior to scanning. On the day of scanning, the cells were incubated with a 3 μM solution of the acetoxymethylester form of an intracellular calcium indicator (either Fluo-4 AM or Fluo-3 AM) in the base media for 25 minutes. The plasma membrane is permeable to the acetoxymethylester forms of Fluo-3 and Fluo-4, which are modified intracellularly by esterases to an impermeable form. The loading solution was also supplemented with 200 ng/ml Hoechst 33342 to label DNA within the nuclei. This concentration of Hoechst provides adequate label of the nuclei and was non-toxic under these conditions. Thus, the labeling procedure introduced a green-fluorescence channel fluorescent calcium indicator into the cytoplasm of the NRVMs (Fluo-4) and a blue-fluorescence channel nuclear stain (Hoechst). The nuclear channel was used for autofocus at each well; additionally, images obtained of the nuclei provided information regarding cellular position that was helpful in assigning boundaries between cells in the segmentation procedure applied to the green-channel images. Following loading, cells were placed in 150 μl of HEPES-buffered physiological saline (Tyrodes solution) supplemented with 5-mM glucose and 2-mM calcium chloride.

This example is merely illustrative and is not intended to limit the application of the principles set forth above to automated measurement and analysis of calcium transients in cardiomyocytes. Other applications may include stem cell, cardiac myocytes derived from stem cells (both embryonic stem cells and induced pluripotent stem cells), neurons, pancreatic beta-cells, adrenal cells, and PC12 cells (which are neuronal like, but derived from the adrenals). In addition to electric signals, stimuli to provoke transient response may include chemicals (e.g., potassium chloride), calcium channel activators (e.g., BayK8644), pressure, light, and sound. Other transients to be measured may include membrane potential across the plasma membrane, membrane potential across the mitochondrial membrane, intracellular sodium, and intracellular potassium.

Exemplary systems which can be used in the practice of the detailed description given above include the high content screening system, the EIDAQ 100 (Q3DM, San Diego, Calif.) which is functionally identical to the later-released Beckman Coulter IC 100. The EIDAQ 100 includes: 1) an inverted epifluorescence microscope (Nikon Eclipse TE2000-U), 2) an intensity-feedback stabilized 100 W Hg arc lamp developed by Q3DM, 3) excitation and emission filter wheels, 4) a motorized stage with XY-axes control, 5) a piezoelectric Z-axis control for fast, precise autofocus, and 6) the software sold by Vala Sciences, Inc. under the CytoShop™ brand. The emission light path on the EIDAQ 100 is split by a Nikon multimode module to the autofocus and scientific grade CCD cameras. The EIDAQ 100's scientific grade camera was removed from the optical path but left powered on and connected to allow normal operation of CytoShop™ software.

Instrumentation according to FIG. 6 was built using a PC running Windows XP and control software programmed in Labview 8.0, (National Instruments, Austin, Tex.), a National Instruments data acquisition I/O board, the NI-PCI-6251, a stimulator/electrode assembly (lowered and raised using a computer-controlled Sutter Instruments (Novato, Calif.) micromanipulator, the MP-285), a Grass Technologies (West Warwick, R.I.) S48 square pulse stimulator, and a high speed scientific-grade CCD camera. Back- and front-illuminated EMCCD cameras were tested including the iXon DU-897 from Andor (South Windsor, Conn.), the ImagEM C9100-13 from Hamamatsu (Hamamatsu, Japan), and the QuantEM from Roper/Photometrics (Tuscon, Ariz.).

The scope of patent protection afforded the novel tools and methods described and illustrated herein may suitably comprise, consist of, or consist essentially of any combination of the elements described above. Further, the novel tools and methods disclosed and illustrated herein may suitably be practiced in the absence of any element or step which is not specifically disclosed in the specification, illustrated in the drawings, and/or exemplified in the embodiments of this application. Moreover, although the invention has been described with reference to presently preferred embodiments, it should be understood that various modifications can be made without departing from the spirit of the invention.

The invention claimed is:

1. A computer executed method for measuring transient activity in cells, comprising the computer-executed steps of:
   acquiring a time-series sequence of magnified images of cells exhibiting transient activity;
   generating a time-series average image from the time-series sequence of magnified images;
   generating cell periphery masks using the time-series average image;
   obtaining measurements of transient activity intensities on a cell-by-cell basis by applying the cell periphery masks to the sequence of magnified images; and,
   generating transient magnitude points representing the transient activity based upon the measured transient activity intensities.

2. The computer executed method of claim 1, wherein acquiring a time-series sequence of magnified images includes:
   autofocusing an objective;
   operating a camera shutter optically coupled to the objective; and then,
   applying a stimulation signal to the cells.

3. The computer executed method of claim 2, wherein applying a stimulation signal includes applying light, pressure, electrical potential, or material to the cells.

4. The computer executed method of claim 2, wherein applying a stimulation signal includes coupling an electrical voltage to the cells.

5. The computer executed method of claim 4, wherein coupling an electrical voltage to the cells includes coupling the electrical voltage by means of electrodes.

* * * * *